United States Patent [19]

Leadbetter

[11] 4,170,601
[45] Oct. 9, 1979

[54] METHOD FOR ISOLATING INSECT SEX PHEROMONES

[76] Inventor: Graham Leadbetter, 9340 Edmonston Rd., Greenbelt, Md. 20770

[21] Appl. No.: 795,277

[22] Filed: May 9, 1977

[51] Int. Cl.² .......................... C09F 5/10; C11B 3/00; C07C 69/00; C07C 97/16; C07C 83/00
[52] U.S. Cl. .................. 260/428.5; 260/419; 260/601 R; 260/593 P; 260/594; 260/465.9; 260/652 P; 260/561 R; 260/561 P; 260/561 S; 260/561 N; 260/561 B; 260/555 C; 260/552 R; 260/583 E; 260/583 EE; 260/583 F; 260/583 H; 260/583 N; 260/584 R; 260/609 C; 260/609 B; 560/147; 560/155; 560/218; 562/554; 562/580; 562/555; 568/917; 568/693
[58] Field of Search .......... 260/412.8, 428.5, 410.9 R, 260/419, 601 R, 593 P, 465.9, 643 A, 652 P, 552 R, 555 C, 561 R, 561 P, 561 N, 561 B, 526 R, 583 N, 583 E, 583 EE, 583 F, 583 H, 609 C, 609 B, 616; 560/155, 218, 147; 562/554, 580, 555; 568/917, 693

[56] References Cited
PUBLICATIONS

Butenandt, A., et al., Liebigs Ann. Chem. 658 39(1962).
Schlenk et al., *J. Am. Chem. Soc.*, vol. 72, pp. 5001–5004 (1950).
Chemical Abstracts, vol 65:4213y.
Chemical Abstracts, vol. 72:33516n.
Chemical Abstracts, vol. 61:2053g.
Swern, D. et al., J. Am. Chem. Soc., 74, pp. 655–657 (1952).

*Primary Examiner*—John F. Niebling
*Attorney, Agent, or Firm*—James J. Brown

[57] ABSTRACT

The isomers of synthetic insect sex pheromones or their precursors are separated by selectively forming an inclusion complex with the E-isomer and urea or thiourea. In order for the E-isomer complex to form selectively it is necessry that the mono-olefin which forms the complex have a primary, linear chain of at least 7 atoms, a molecular diameter of 2.8-6Å, and a polar functional group having transverse dimensions of less than 6Å. Branching between the olefinic bond and the polar functional group is limited to methyl groups.

7 Claims, No Drawings

METHOD FOR ISOLATING INSECT SEX PHEROMONES

BRIEF DESCRIPTION OF INVENTION

The present invention is concerned with the isolation of biologically active synthetic insect sex-attractants known as sex pheromones. Specifically the invention is concerned with a method of separating the geometric isomers of certain mono-olefins in order to obtain biologically active sex pheromones or the synthetic precursors, wherein an inclusion complex is selectively formed with urea or thiourea and one of the gometric isomers.

BACKGROUND OF THE INVENTION

The efficient control of insects has long presented man with a vexatious problem, particularly with respect to insects which compete with man for food supplies and other vegetable material or contribute to the spread of disease. The twin concerns of world wide hunger and recent awareness of environmental and health effects from the use of chemical insecticides has further compounded this ancient problem.

With the realization that many of the chemicals which have been used to control insects are toxic not only to the insects themselves but to man as well, attention has been focused on other means of effecting control of insects which do not possess environmentally objectionable characterics.

One area of recent interest has been the isolation, extraction or synthesis of substances which are secreted by insects of one sex to attract the insect of the opposite sex. Combined with suitable means for either traping and destroying the insects or interfering with their reproductive cycle, these substances offer a future hope of controlling insect populations in an environmentally acceptable manner.

Unfortunately, although the substances secreted as sex pheromones by various insects can be identified, obtaining them is useful quantities has proven difficult. The amount of attractant actually secreted by the insect is extremely small—in the order of nanograms—thereby effectively precluding the insects themselves as a natural sources for the material. In addition, synthetic means for isolating insect sex pheromones have proven to be difficult and expensive.

Naturally occuring insect sex pheromones are known to possess generally a common molecular structure of a linear chain of carbon atoms with one or more double bonds and a remote functional group such as an acetate ester or aldehyde. These compounds can take several isomeric forms and it is recognized that the relative proportions of the respective geometric isomers are critical to their function as insect sex pheromones.

Unfortunately the preparation of the individual isomers chemically or their separation from a mixture has heretofore been both difficult and expensive, thereby effectively precluding production of these pheromones synthetically at attractive cost and in suitable quantities for commercial use.

While the prior art has suggested the formation of inclusion complexes as a means for carrying out some chemical separations of organic compounds, it has not previously been recognized or suggested that synthetic insect sex pheromones could effectively be isolated in this manner. More specifically and with particular regard to compounds having the structural characteristics of insect sex pheromones there has not been a recognition of a structural relationship between the dimensions of the inclusion complex and the size and position of functional groups which relationship would permit separation of the geometric isomers.

Examples of prior work in this area generally are as follows:

DISCUSSION OF PRIOR ART

Butenandt et al., *Ann. Chem.* 658, 39 (1962) have suggested the general use of urea in multi-stage separations of olefin isomers without distinguishing between mono and diolefins or indicating the significance of functional groups on the olefin.

Coleman et al., *J. Am. Chem. Soc.* 4886, 74 (1952) have employed urea complexes to separate methyl oleate from peroxides.

Schlenk and Holman, *J. Am. Chem. Soc.* 72, 5001 (1950) have disclosed the separation of a series of saturated acids from unsaturated acids by forming a urea inclusion complex with the saturated acid.

Trutter, *J. Chem. Soc.* 2416, (1951) has recognized the necessity of certain structural features in saturated and unsaturated compounds for urea inclusion complexes to form. Specifically, it is disclosed that certain chain lengths are necessary depending on degree of type of branching. It is also recognized that normal esters form complexes under some conditions while benzoates do not.

Swern et al., *J. Am. Chem. Soc.* 74, 1655 (1952) disclose the use of urea complexes to separate erythro and threo 9, 10-dihydroxy stearic acids.

The prior art has not, however, suggested the specific separation of the geometric isomers of compounds having the structure of insect sex pheromones by selectively forming urea or thiourea inclusion complexes with one of the isomers, nor has it recognized the unique influence of remote functional groups of the isomers in the formation of such complexes.

OBJECTS OF THE INVENTION

It is therefore an object of the present invention to provide a method for effectively separating the E and Z geometric isomers of mono-olefins having the structure of insect sex pheromones of their precursors.

It is further object of the present invention to provide a method for separating the isomers of these monolefins which relies upon the relationship which has been found between inclusion complex formation and remote functional groups on the mono-olefin.

DETAILED DESCRIPTION OF THE INVENTION

According to the present invention, it has been found that the E and Z isomers of certain mono-olefins having the structural characteristics of insect sex pheromones or the precursors of these pheromones can be separated by selectively forming an inclusion complex with urea or thiourea and the E isomer of the mono-olefin. More specifically it has been found that the position and dimensions of the functional group remote from the double bond of the mono-olefin as well as other structural features of the molecule profoundly influence the ability of the compound to form selectively the complex and thereby to be separated into respective E and Z isomeric fractions.

The present invention resides primarily in the discovery that the functional group located in a certain relationship to the olefinic bond must possess certain dimensions in order for an inclusion complex either to be formed at all or to be formed selectively with either urea or thiourea. Thus, according to the invention, an inclusion complex is selectively formed between either urea or thiourea and the E-isomer of a monolefin characterized by a primary linear chain of at least 7 atoms which has a molecular diameter of about 2.8 to 6 Å and the linear atoms comprise carbon atoms and optionally 1 or 2 non-adjacent, linear hetero atoms selected from nitrogen, oxygen, sulfur and phosphorus. At least one, polar functional group must be present having dimensions transverse to said linear chain of less than 6 Å. The only branching (other than the functional group itself) which can be present on the primary linear chain between the functional group and the olefinic bond are methyl groups. Where each of the olefinic carbon atoms has only a hydrogen atom present on it (aside from its bond with the other atoms of the linear chain), the functional group is preferably limited to a transverse size of less than 2.83 Å. Where only one of the olefinic carbon atoms contains a single hydrogen, the transverse dimensions of the functional group are preferably between 2.83 and 6 Å.

While not wishing to be bound by theory, it is believed that complex formation does not occur if the functional group of the linear chain exceeds 6 Å in lateral dimensions because the group is too large to fit within the helical structure of the urea. On the other hand, if the lateral dimensions of the primary, linear chain is smaller than 2.8 Å, no complex forms either because the lateral dimensions of the chain are too much smaller than the complex.

Although not an exclusive listing, functional groups which have been found to be satisfactory in selectively forming E-isomer complexes are:

|  | A |
| --- | --- |
| Aldehyde | 2.1 |
| Nitrile | 2 |
| Alcohol | 2.8 |
| Bromine | 2.0 |
| Ester | 2.1–4.5* |
| Amine | 1.8 |
| Dimethyl amine | 4.0 |
| Methyl keto | 3.5 |
| Ethyl ketone | 4.1–2* |
| Methyl | 2.0 |

*depending on rotational configuration

Additional functional groups which can be employed according to the invention are: other halides, amides such as urea and thiourea, mercaptans, thioethers, ethers, carboxyls and carbamates.

Neither total linear chain length or degree of branching beyond the functional group are critical according to the present invention. While a total linear chain of at least 7 atoms is required to form the complex, the chain may possess any additional length since this merely results in extensions of the length of the helical structure which forms the inclusion complex. Similarly, branching on the carbon atoms between the remote end of the chain adjacent the olefinically bonded carbon and the functional group is limited to hydrogen and methyl groups in the case of urea and hydrogen, methyl or ethyl groups in the case of thiourea.

It is further theorized that selective complexing occurs according to the invention because in the E-isomer, where the proper relationship exists between the functional group and the linear chain, the functional group hydrogen bonds with the urea complex and influences the size of the channel in the helix to permit insertion of the linear chain. Thus, to achieve effective complex formation and separation, in the case of trisubstituted olefin (i.e. in which a single hydrogen atom is found on only one of the olefinic carbons and a branched methyl substituent is present on the other) a relatively large functional group is needed to provide a channel sufficiently large i.e. in the order of about 5 Å. In the case of disubstituted olefins (i.e. where a single hydrogen atom is present on both olefinic carbons and there is therefore no side branching on either carbon), however, a smaller channel is required and therefore a functional group having a cross section of less than 2.8 Å is effective.

While the E-isomers of olefins having the described structural characteristics form inclusion complexes with urea and thiourea under the specified conditions, the Z-isomer which is not linear, does not, thereby permitting the desired separation of the isomeric fractions.

Since the guest olefin is physically rather than chemically bound in the urea or thiourea complex, the "reaction" is non-stoichiometric and the amount of urea becomes greater as the linear length of the olefin increases since the helix merely grows in length to accommodate the longer molecule.

Selective formation of the E-isomer inclusion complex can conveniently be carried out at room temperature in a suitable solvent for the urea or thiourea and olefin. Suitable solvents include methanol, ethanol, propanal, i-propanol, dimethyl formamide, dimethyl sulfoxide and other polar organic solvents capable of dissolving urea or thiourea. The complexed isomer, on standing, will take the form of crystals which can be separated from the remaining solution by familiar techniques such as filtration or centrifuging. The solution remaining after separation of the crystals contains the non-complexed Z-isomer, while the crystals themselves are the complexed E-isomer. The E-isomer-inclusion complex may then be dissolved in water to produce an organic and an aqueous phrase. Separation and drying of the organic phase gives pure E-isomer in those cases where selective complexing took place.

The following examples further illustrate the practice of the present invention:

EXAMPLE I

A solution of 119 g. of urea (1.98 m.) in 600 ml. of methanol was treated with 33.7 g (0.14 m.) of 11-hexadecenal. Crystals appeared immediately. The solution was allowed to stand and then the crystals were filtered and washed with ether. The filtrate and washings were evaporated to dryness on a rotatory evaporator. The residue was washed with petroleum ether (2×200 ml.) and filtered. This solution now contained the pure Z iosmer. The crystals after washing were combined with the first crop.

Isolation of E-isomer.

The combined crystals were dissolved in 400 ml. of water, the upper organic layer separated, and the aqueous layer extracted with 2×200 ml. hexane. The combined organic phase was washed with 75 ml. of water, dried over $MgSO_4$, filtered and evaporated to give 14.4 g. of the E-isomer.

Isolation of Z-isomer.

The petroleum ether solution which contained the Z isomer was evaporated to give 15.5 g. of pure Z-isomer.

EXAMPLE 2

Separation of methyl 4 heptenenoates into the individual E and Z-isomers.

The mixed ester (24.7 g.) was treated with 70 g. of urea in 300 ml. of methanol and allowed to stand overnight. A mixture of crystals and solution formed and the solution was evaporated on a rotatory evaporator and the crystalline residue washed with 2×200 ml. portions of petroleum ether. Filtration and evaporation of the petroleum ether gave 16.6 g. of the Z-isomer.

E-isomer.

The crystaline urea was dissolved in 250 ml. of water. Extraction of the aqueous solution was 2×200 ml. of diethyl ether, drying over MgSO$_4$, filtration and evaporation of the ether gave 2.4 g. of E-isomer.

EXAMPLE 3

Separation of methyl 4-nonenoates into the individual E and Z isomers.

The isomeric mixture (48.5 g.) was treated with 140 g. of urea in 700 ml. of methanol and allowed to stand overnight. A mixture of crystals and solution formed and the methanol was removed on the rotatory evaporator and the crystalline residue washed with 2×200 ml. of petroleum ether. Filtration and evaporation of the petroleum ether gave 42.1 g. of Z-isomer.

E-isomer.

The urea complex residue was dissolved in 500 ml. of water, the aqueous solution extracted with 2×200 ml. of diethyl ether. The ether was dried over MgSO$_4$, filtered and evaporated to give 1.0 g. of the E-isomer.

EXAMPLE 4

Separation of 11-hexadecenals into the individual E and Z-isomers.

A solution of 110 g. of urea (1.98 m) in 600 ml. of methanol was treated with 33.7 g. (0.14 m) of 11-hexadecenal. Crystals appeared immediately. The solution and crystals were allowed to stand and then the crystals were filtered and washed with ether. The filtrate and washings were evaporated to dryness on a rotatory evaporator. The crystalline residue was washed with petroleum ether (2×200 ml.) and filtered. This solution now contained the pure Z isomer. The crystals after washing were combined with the first crop of crystals.

Isolation of Z-isomer.

The petroleum ether was evaporated to give 15.5 g. of pure Z-isomer.

Isolation of E-isomer.

The combined crystals were dissolved in 400 ml. of water, the upper organic layer separated, and the aqueous layer was extracted with 2×200 ml. hexane. The combined organic phase was washed with 75 ml. of water, dried over MgSO$_4$, filtered, and evaporated to give 14.4 g. of E. isomer.

EXAMPLE 5

Separation of methyl 12-methyl-11-pentadecenoates into the individual E and Z-isomers.

The mixed esters (81.4 g.) were treated with 135 g. of urea dissolved in 850 ml. of methanol and allowed to stand for 3 hours. A mixture of crystals and solution formed. The methanol solution was concentrated to dryness and the crystalline urea residue was extracted with two 200 ml. portions of petroleum ether. Filtration and evaporation of the petroleum ether gave 60.0 g. of the Z-isomer. The process was repeated two more times till glc analysis (EGS-SX Scott Column) showed no E-isomer, yield of Z isomer 48 g. Treatment of another preparation of 100 g. of mixture with 156 g. of urea and 850 ml. of methanol which was allowed to stand overnight gave 31 g. of the Z-isomer which showed no E-isomer present.

E-isomer.

The urea complex was dissolved in 500 ml. of water. The complex decomposed to give two phases. The upper organic phase was separated, and the lower aqueous phase was extracted with two portions of 200 ml. of petroleum ether. The combined organic phases were dried over magnesium sulfate, filtered and evaporated at reduced pressure to give 28.8 g. GLC analysis showed no Z-isomer present.

EXAMPLE 6

Separation of 9-tetradecenols into the individual E and Z-isomers.

Urea (10.0 g.) in 100 ml. of methanol was added to 27.5 G. of 9-tetradecenol and allowed to stand at room temperature for 16 hours. A mixture of crystals and solvent formed. The solvent was evaporated and the residue extracted with two 200 ml. portions of petroleum ether and filtered. Evaporation of the petroleum ether gave 23.2 g. of the Z-isomer. Liquid chromatography showed the ratio of Z/E isomers was 97.6/2.4.

EXAMPLE 7

Separation of 9-tetradecenenitriles into the individual E and Z-isomers.

The mixed nitriles (20.8 g.) were treated with 60 g. urea in 300 ml. of methanol and let stand for 1 hour. A mixture of crystals and solutions formed. The methanol was evaporated from the mixture and the residue of urea complex washed with 200 ml. of hexane (two times) and the hexane extracts filtered and evaporated to give 16.8 g. of the Z-isomer.

E-isomer.

The urea complex was dissolved in 250 ml. of water, the upper organic phase separated, the aqueous phase extracted with 2×200 ml. portions phase, washed with 50 ml. water, dried over MgSO$_4$, filtered and evaporated to give 3.0 g. of the E-isomer.

EXAMPLE 8

Separation of 4-nonene bromide into the individual E and Z-isomers.

The isomeric mixture (13.0 g.) was treated with 25 g. urea in 100 ml. of methanol and allowed to stand overnight to form crystals and solution. The methanol was evaporated from the mixture and the residue extracted with 2×200 ml. of petroleum ether. Filtration and evaporation of the petroleum ether gave 9.35 g. of Z-isomer.

E-isomer.

The urea complex was dissolved in 50 g. of water. The aqueous solution was extracted with 2×200 ml. of diethyl ether. Drying the ether over MgSO$_4$, filtration and evaporation gave 800 mg. of the E-isomer.

I claim:

1. A method of separating a mixture of E and Z isomers of mono-olefins suitable for use as insect sex pheromones or the preparation thereof which comprises reacting said mixture of E and Z isomers with urea to form an inclusion complex with the E isomer and separating said E isomer complex from said Z isomer; said mono olefins being characterized by having a primary linear chain of at least 7 atoms consisting of carbon atoms, or carbon atoms and 1-2 non-adjacent, linear hetero atoms selected from the group consisting of N, O, S and P and having a molecular diameter of 2.8 to 6 Å, at least one terminal functional group having dimensions transverse to said linear chain of 2.83 to 6 Å, hydrogen or methyl groups only being present as branches on said primary linear chain of 7 atoms and between said terminal group and the olefinically bonded atoms, and a single hydrogen atom being present on only one of said olefinically bonded atoms with a single methyl group being present on the other.

2. The method of claim 1 wherein said terminal functional group is selected from the group consisting of an ester, aldehyde, ketone, nitrile, alcohol, halogen, amide, carboxylic acid, amine, mercaptan, thioether, ether, and carbamate.

3. The method of claim 2 wherein said amide is urea or thiourea.

4. The method of claim 1 wherein said E-isomer forms a crystalline inclusion complex with the urea while the Z-isomer remains dissolved in liquid reaction media.

5. A method of separating a mixture of E and Z isomers of mono-olefins suitable for use as insect sex pheromones or the preparation thereof which comprises reacting said mixture of E and Z isomers with urea to form an inclusion complex with the E isomer and separating said E isomer complex from said Z isomer; said mono-olefins being characterized by having a primary linear chain of at least 7 atoms consisting of carbon atoms, or carbon atoms and 1-2 non-adjacent, linear hetero atoms selected from the group consisting of N, O, S, and P and having a molecular diameter of 2.8 to 6 Å, at least one terminal functional group having dimensions transverse to said linear chain of less than 2.83 Å, hydrogen or methyl groups only being present as branches on said primary linear chain of 7 atoms and between said terminal group and the olefinically bonded atoms, and a single hydrogen atom being present on each of said olefinically bonded atoms.

6. The method of claim 5 wherein said terminal functional group is selected from the group consisting of an ester, aldehyde, ketone, nitrile, alcohol, halogen, amide, carboxylic acid, amine, mercaptan, ether, and carbamate.

7. The method of claim 5 wherein said E-isomer forms a crystalline inclusion complex with the urea while the Z-isomer remains dissolved in liquid reaction media.

* * * * *